US009648875B2

(12) United States Patent
Koenig et al.

(10) Patent No.: US 9,648,875 B2
(45) Date of Patent: May 16, 2017

(54) SPORICIDAL FORMULATION INCLUDING AMINE OXIDE SURFACTANT AND A MIXTURE OF OXIDANTS

(75) Inventors: David William Koenig, Menasha, WI (US); Douglas Robert Hoffman, Greenville, WI (US); Yang Huang, Jiangsu (CN); Aimin He, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 336 days.

(21) Appl. No.: 14/347,446

(22) PCT Filed: Oct. 28, 2011

(86) PCT No.: PCT/CN2011/001810
§ 371 (c)(1),
(2), (4) Date: Jan. 5, 2015

(87) PCT Pub. No.: WO2013/059970
PCT Pub. Date: May 2, 2013

(65) Prior Publication Data
US 2015/0110893 A1   Apr. 23, 2015

(51) Int. Cl.
| | |
|---|---|
| *A01N 33/24* | (2006.01) |
| *A01N 59/00* | (2006.01) |
| *A01N 37/16* | (2006.01) |
| *A01N 37/10* | (2006.01) |
| *A01N 25/06* | (2006.01) |
| *A01N 25/30* | (2006.01) |
| *A47K 10/32* | (2006.01) |
| *A61K 8/02* | (2006.01) |
| *A61K 9/70* | (2006.01) |
| *A61Q 17/00* | (2006.01) |
| *A01N 25/08* | (2006.01) |

(52) U.S. Cl.
CPC ............. *A01N 33/24* (2013.01); *A01N 25/08* (2013.01); *A01N 37/10* (2013.01); *A01N 59/00* (2013.01); *A61K 8/0208* (2013.01); *A61K 9/7007* (2013.01); *A61Q 17/005* (2013.01); *A47K 2010/3266* (2013.01)

(58) Field of Classification Search
CPC ........ A01N 33/24; A01N 37/10; A01N 25/08; A01N 59/00; A01N 25/30; A01N 37/16; A47K 2010/3266; A61K 8/0208; A61K 9/7007; A61Q 17/005
See application file for complete search history.

(56) References Cited

U.S. PATENT DOCUMENTS

| | | |
|---|---|---|
| 4,100,324 A | 7/1978 | Anderson et al. |
| 5,284,703 A | 2/1994 | Everhart et al. |
| 5,350,624 A | 9/1994 | Georger et al. |
| 6,010,993 A | 1/2000 | Romano et al. |
| 6,048,836 A | 4/2000 | Romano et al. |
| 6,168,808 B1 | 1/2001 | Hamon Godin et al. |
| 6,235,699 B1 | 5/2001 | Del Duca et al. |
| 6,444,230 B1 | 9/2002 | Godin et al. |
| 6,479,454 B1 | 11/2002 | Smith et al. |
| 6,534,075 B1 | 3/2003 | Hei et al. |
| 6,627,593 B2 | 9/2003 | Hei et al. |
| 6,627,657 B1 * | 9/2003 | Hilgren .................. A01N 37/16 514/553 |
| 6,946,413 B2 | 9/2005 | Lange et al. |
| 7,708,905 B2 | 5/2010 | Lee et al. |
| 8,563,017 B2 | 10/2013 | Cunningham et al. |
| 2003/0175318 A1 | 9/2003 | Schilling et al. |
| 2004/0171687 A1 | 9/2004 | Kemp et al. |
| 2005/0152991 A1 | 7/2005 | Man et al. |
| 2006/0008621 A1 | 1/2006 | Gusky et al. |
| 2006/0113506 A1 | 6/2006 | Man et al. |
| 2006/0233886 A1 | 10/2006 | Kielbania, Jr. et al. |
| 2006/0251749 A1 | 11/2006 | Jia et al. |
| 2009/0285871 A1 | 11/2009 | Cunningham et al. |
| 2011/0223267 A1 | 9/2011 | Jia et al. |

FOREIGN PATENT DOCUMENTS

| | | |
|---|---|---|
| CN | 1207121 | 2/1999 |
| CN | 1222933 | 7/1999 |
| CN | 1229335 | 9/1999 |
| CN | 1252093 | 5/2000 |
| CN | 1299678 | 6/2001 |

(Continued)

OTHER PUBLICATIONS

Zeng, et al., "Application of a novel bleach activator to low temperature bleaching of raw cotton fabrics", The Journal of the Textile Institute, Taylor & Francis, vol. 106, No. 8, Jan. 1, 2015, pp. 807-813.
European Search Report and Opinion for EP11874463.0, dated Apr. 28, 2015.
European Search Report and Opinion for EP11874768.2, dated Apr. 28, 2015.
Feng et al., "Applications of microcalorimetry in the antibacterial activity evaluation of various Rhizoma coptidis," Pharmaceutical Biology, vol. 49, No. 4, Apr. 1, 2011, pp. 348-353.
Wang et al., "The mechanism of neogambogic acid-induced apoptosis in human MCF-7 cells," Acta Biochimica et Biophysica Sinica, vol. 43, No. 9, Jul. 23, 2011, pp. 698-702.

(Continued)

*Primary Examiner* — John Pak
*Assistant Examiner* — Nathan W Schlientz
(74) *Attorney, Agent, or Firm* — Kimberly-Clark Worldwide, Inc.

(57) ABSTRACT

Formulations and wipes for imparting a sporicide to a surface are disclosed herein. To achieve the sporicidal efficacy of the product, a synergistic amount of an amine oxide surfactant and a mixture of oxidants is incorporated into the formulation. The operative sporicidal formulation contains a solvent, an amine oxide surfactant, a water soluble oxidant and a water insoluble oxidant. Typically, the formulation can contain about 0.05 to about 3.7 percent (by weight of the formulation) of an amine oxide surfactant, about 0.5 to about 4 percent (by weight of the formulation) of a water soluble oxidant, and about 0.1 to about 6 percent (by weight of the formulation) of a water insoluble oxidant.

10 Claims, No Drawings

(56) References Cited

FOREIGN PATENT DOCUMENTS

| | | |
|---|---|---|
| CN | 1670158 | 9/2005 |
| CN | 101129457 | 2/2008 |
| CN | 101278929 | 10/2008 |
| CN | 101810336 | 8/2010 |
| CN | 102027169 | 4/2011 |
| CN | 102166177 | 8/2011 |
| CN | 102205022 | 10/2011 |
| EP | 0873687 | 10/1996 |
| EP | 0779357 | 6/1997 |
| EP | 0805198 | 11/1997 |
| EP | 1447100 | 8/2004 |
| JP | H01-172341 | 7/1989 |
| KR | 20110051492 | 5/2011 |
| WO | WO 96/17044 | 6/1996 |
| WO | WO 00/57730 | 10/2000 |
| WO | WO 03/005817 | 1/2003 |
| WO | WO 2005/095323 | 10/2005 |
| WO | WO 2006/122160 | 11/2006 |

OTHER PUBLICATIONS

Xu et al., "A novel antifungal peptide from foxtail millet seeds," Journal of the Science of Food and Agriculture, vol. 91, No. 9, Mar. 28, 2011, pp. 1630-1637.

Wang, Ling et al. Studies on Antifungal Activity of Extracts from Six Traditional Chinese Medicines against Dematophyte Genus, Chin. J. Derm. Venereol. Aug. 2008, vol. 22, No. 8, pp. 498-500. (With English Abstract).

Zhang, Ning et al. Clinical and Laboratory Research on the Therapeutical Effect Gacinia Morella Desv (GMD) in Genital Herpes. Chin. J. Dermatol, Jun. 2000, vol. 33, No. 3, pp. 167-168. (With English Abstract).

Guo, Zinchun et al, Screening of 20 Kinds of Chinese Herbs Extracts for Antifungal Activity. Journal of Jiangxi Normal University (Natural Science), Mar. 2007. vol. 31, No. 2, pp. 161-163. (With English Abstract).

Wang, Qianwen et al. Screen of Studies on Antifungal Activity of Ethanol Extracts from 89 Traditional Chinese Medicines. Journal of Zhejian University of Technology. Jun. 2009, vol. 37, No. 3, pp. 289-294. (With English Abstract).

Chen, Yufeng et al. Experimental Treatment Using Combined Fructus Psoraleae and Dihydroartemisinin in Mouse Cryptospordiosis. Chin. J. Parasitol Parasit. Dis. Feb. 2008, vol. 26, No. 1, pp. 67-69. (With English Abstract).

International Preliminary Report on Patentability, PCT/CN2011/001809.

International Search Report, PCT/CN2011/001809.

International Preliminary Report on Patentability, PCT/CN2011/001810.

International Search Report, PCT/CN2011/001810.

* cited by examiner

SPORICIDAL FORMULATION INCLUDING AMINE OXIDE SURFACTANT AND A MIXTURE OF OXIDANTS

RELATED APPLICATION

This application is based on and claims priority to International Application No. PCT/CN2011/001810 filed on Oct. 28, 2011, which is incorporated herein by reference in its entirety.

BACKGROUND

Spores are metabolically dormant microbes that remain viable under a wide range of environmental conditions. Spores are typically heat-, acid-, and desiccation-resistant and can persist in the environment for years. Because of their stability, contamination by spores is very common in hospital, clinical, long-term care or nursing home environments. Often, it can be cultured from almost any surface in a hospital. Patient-to-patient transmission of spores occurs by sharing the medical equipment or facilities in hospitals, nursing homes, and other extended-care facilities. Transmission in community settings also occurs.

Given the pathogenesis of various spore-forming microorganisms, judicious use of antibiotics and strict infection control and environmental measures are keys to the prevention and outbreak of disease. The implementation of antibiotic stewardship programs has been associated with decreased incidence of spore related diseases. To prevent spread of spores, environmental cleaning and patient isolation are needed. Several disinfectants commonly used in hospitals may be ineffective against spores, and may actually promote spore formation.

For example, *Clostridium difficile*, also known as "CDF/cdf", or "*C. diff*", a species of gram-positive, spore-forming anaerobic bacillus, can lead to severe complications ranging from antibiotic-associated diarrhea to severe life-threatening pseudomembranous colitis, a severe infection of the colon. In fact, *C. diff*. is the cause of approximately 25 percent of all cases of antibiotic-associated diarrhea. Most cases of *C. diff*. associated disease occur in hospitals or long-term care facilities causing more than 300,000 cases per year in the United States alone. The total US hospital costs for *C. diff*. associated disease management have been estimated to be $3.2 billion per year.

Health care workers should avoid using only alcohol hand sanitizers, especially in *C. diff* outbreaks, because alcohol is not effective at killing spores. Due to their resistant nature, spores are very difficult to eliminate with standard measures. Consumer and health care applications are taking measures with large amounts of harsh chemicals including ethylene oxide, aldehydes and highly reactive oxidizing agents such as peracetic acid, chlorine dioxide and ozone which are either carcinogenic or corrosive. It would be virtually impossible to use the current technologies/tactics on skin and delicate devices or surfaces. There is a need to develop a sporicide disinfectant that is nonharmful to human skin and the environment but still provides the sporicidal efficacy.

SUMMARY

Generally stated, formulations and wipes for imparting a sporicide to a surface are disclosed herein. To achieve the sporicidal efficacy of the product, a synergistic amount of an amine oxide surfactant, a water soluble oxidant and a water insoluble oxidant is incorporated into the formulation.

The operative sporicidal formulation contains a solvent, an amine oxide surfactant, a water soluble oxidant and a water insoluble oxidant. Typically, the formulation can contain about 0.05 to about 3.7 percent (by weight of the formulation) of an amine oxide surfactant, about 0.5 to about 4 percent (by weight of the formulation) of a water soluble oxidant, and about 0.1 to about 6 percent (by weight of the formulation) of a water insoluble oxidant.

The amine oxide surfactant is selected from lauramine oxide, alkyldimethyl amine oxide, cocodimethylamine oxide, tetradecyldimethyl amine oxide, almondamidopropylamine oxide, babassuamidopropylamine oxide, behenamine oxide, cocamidopropylamine oxide, cocamine oxide, decylamine oxide, decyltetradecylamine oxide, dihydroxyethyl $C_{8-10}$ alkoxypropylamine oxide, dihydroxyethyl $C_{9-11}$ alkoxypropylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12-15}$ alkoxypropylamine oxide, IPDI/PEG-15 soyamine oxide, copolymerisostearamidopropylamine oxide, lauramidopropylamine oxide, lauramine oxide, milkamidopropyl amine oxide, minkamidopropylamine oxide, myristamidopropylamine oxide, myristamine oxide, myristyl/cetyl amine oxide, oleamidopropylamine oxide, oleamine oxide, olivamidopropylamine oxide, palmitamidopropylamine oxide, palmitamine oxide, PEG-3 lauramine oxide, potassium dihydroxyethyl cocamine oxide phosphate, potassium trisphosphonomethylamine oxide, sesamidopropylamine oxide, soyamidopropylamine oxide, stearamidopropylamine oxide, stearamine oxide, tallowamidopropylamine oxide, tallowamine oxide, trimethylamine oxide, undecylenamidopropylamine oxide, wheat germamidopropylamine oxide, and combinations thereof. In one desirable sporicidal formulation, the amine oxide surfactant may be lauramine oxide.

Suitable water soluble oxidants are selected from hydrogen peroxide, hypochlorous acid, chlorine, hypoiodous acid, hypobromite, hypobromous acid, bromine, iodine, chlorine dioxide, ozone, superoxide, electrolyzed water, ammonium persulfate, potassium bromate, potassium caroate (mixture of potassium monopersulfate, potassium sulphate, and potassium bisulfate), potassium chlorate, potassium monopersulfate, potassium persulfate, polyvinylpyrrolidone hydrogen peroxide, sodium bromate, sodium caproylethylformyl benzenesulfonate, sodium carbonate peroxide, sodium chlorate, sodium iodate, sodium perborate, sodium persulfate, urea peroxide, and combinations thereof. In one desirable sporicidal formulation, the water soluble oxidant may be hydrogen peroxide. One skilled in the art will appreciate the selection of which water soluble oxidant to utilize will be largely dependent on the desired pH of the final formulation.

As described above, the sporicidal formulation requires a water insoluble oxidant to provide the synergistic effect necessary to treat the spores. Suitable water insoluble oxidants are selected from benzoyl peroxide, lauroyl peroxide, cumene hydroperoxide, dibenzoyl peroxide, t-butyl benzoyl peroxide, ergosterol endoperoxide, strontium peroxide, ozonized turpentine, magnesium peroxide, and combinations thereof. In one desirable sporicidal formulation, the water insoluble oxidant may be benzoyl peroxide. One skilled in the art will appreciate the selection of water insoluble oxidant to utilize will be largely dependent on the desired pH of the final formulation.

DETAILED DESCRIPTION

Generally stated, formulations and wipes for imparting a sporicidal effect to a surface is disclosed herein. To achieve the sporicidal efficacy of the product, a synergistic amount of an amine oxide surfactant and a mixture of a water soluble oxidant and a water insoluble oxidant are incorporated into the formulation. Unexpectedly, despite the difficulty in combating spores with various formulations as described in the past, use of an amine oxide surfactant with a water soluble oxidant and a water insoluble oxidant provides this synergistic effect. An operative sporicidal formulation contains a solvent, an amine oxide surfactant, a water soluble oxidant and a water insoluble oxidant. The synergistic effect specific to the combination of a water soluble oxidant and a water insoluble oxidant with an amine oxide surfactant is an unexpected observation. Advantageously, the sporicidal formulation used herein is not hydrophobic and thus can readily be incorporated into water-based compositions, such as wet wipe compositions.

The sporicidal formulation described herein may be used in combination with a product. The sporicidal formulation may be formulated with one or more conventional pharmaceutically-acceptable and compatible carrier materials to form a personal care delivery composition. The personal care delivery composition may take a variety of forms including, without limitation, aqueous solutions, gels, balms, lotions, suspensions, creams, milks, salves, ointments, sprays, foams, solid sticks, and aerosols. More particularly, the sporicidal formulation may be incorporated into or onto a substrate, such as a wipe substrate, an absorbent substrate, a fabric or cloth substrate, or a tissue substrate, among others. For example, the sporicidal formulation may be incorporated into cleansing products, such as wipes, absorbent articles, cloths, cleaning articles, and the like. More particularly, the sporicidal formulation may be incorporated into wipes such as wet wipes, dry wipes, hand wipes, face wipes, cosmetic wipes, and the like. In one preferred embodiment, the sporicidal formulation is a liquid composition that may be used in combination with a wipe substrate to form a wet wipe, or may be a wetting composition for use in combination with a dispersible wet wipe.

Reference will now be made in detail to the presently preferred embodiments of the invention. Each example is provided by way of explanation and is not meant as a limitation. For example, features illustrated or described as part of one embodiment can be used on another embodiment or figure to yield yet another embodiment. It is intended that the present disclosure include such modifications and variations.

As described above, the sporicidal formulation requires an amine oxide surfactant to provide the synergistic effect needed to provide sporicidal efficacy. An amine oxide, also known as amine-N-oxide and N-oxide, is a chemical compound that contains the functional group $R^3N+$—$O$—, an N—O bond with three additional hydrogen and/or hydrocarbon side chains attached to a nitrogen molecule. Results obtained with other surfactants indicate that there is a specific requirement with respect to the structure of the amine oxide surfactant for obtaining the synergistic effect with the mixture of oxidants.

Amphoteric and nonionic surfactants such as amine oxides have dual functional groups (both acidic and basic groups) in the same molecule. They are electrically neutral but carry both positive and negative charges on different atoms in an aqueous solution. Depending on the composition and conditions of pH value, the substances can have anionic or cationic properties. In the presence of acids, they will accept the hydrogen ions but they will donate hydrogen ions to the solution in the presence of bases, which balances the pH. Such actions make buffer solutions which resist change to the pH. Amphoteric surfactants change their charge according to the pH of the solution, affecting properties of foaming, wetting and detergency through a surface action that exerts both hydrophilic and hydrophobic properties.

Amine oxides are used as a protecting group for amines and as chemical intermediates. Long-chain alkyl amine oxides are used as nonionic surfactants and foam stabilizers. Amine oxides are highly polar molecules and that have a polarity close to that of quaternary ammonium salts. Small amine oxides are very hydrophilic and have excellent water solubility and a very poor solubility in most organic solvents. Amine oxides are weak bases with a pKa of around 4.5 that form $R^3N+$—$OH$, cationic hydroxylamines, upon protonation at a pH below their pKa.

Not to be bound by any theory, but it is believed that disorganization of the spore coat after interaction with the amine oxide surfactant allows for the oxidant(s) to oxidize critical components of the spore making it unable to germinate. Conversely, it is also hypothesized the amine oxide surfactant initiates germination events providing accessible targets for oxidation. It is also possible that both events occur providing an enhanced kill. The amine oxide surfactant by itself does not have a sporicidal efficacy. The oxidants used alone at the concentrations in the formulations described herein also maintains poor sporicidal efficacy. However, when combined with the amine oxide surfactant excellent sporicidal efficacy is achieved.

Suitable amine oxides for use with the sporicidal formulation may include, but are not limited to, lauramine oxide, alkyldimethyl amine oxide, cocodimethylamine oxide, tetradecyldimethyl amine oxide, almondamidopropylamine oxide, babassuamidopropylamine oxide, behenamine oxide, cocamidopropylamine oxide, cocamine oxide, decylamine oxide, decyltetradecylamine oxide, dihydroxyethyl $C_{8-10}$ alkoxypropylamine oxide, dihydroxyethyl $C_{9-11}$ alkoxypropylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12-15}$ alkoxypropylamine oxide, IPDI/PEG-15 soyamine oxide, copolymerisostearamidopropylamine oxide, lauramidopropylamine oxide, lauramine oxide, milkamidopropyl amine oxide, minkamidopropylamine oxide, myristamidopropylamine oxide, myristamine oxide, myristyl/cetyl amine oxide, oleamidopropylamine oxide, oleamine oxide, olivamidopropylamine oxide, palmitamidopropylamine oxide, palmitamine oxide, PEG-3 lauramine oxide, potassium dihydroxyethyl cocamine oxide phosphate, potassium trisphosphonomethylamine oxide, sesamidopropylamine oxide, soyamidopropylamine oxide, stearamidopropylamine oxide, stearamine oxide, tallowamidopropylamine oxide, tallowamine oxide, trimethylamine oxide, undecylenamidopropylamine oxide, wheat germamidopropylamine oxide, and combinations thereof. In one desirable sporicidal formulation, the surfactant is lauramine oxide.

Typically, the sporicidal formulation may contain the amine oxide surfactant in an amount less than about 3.7 percent (by weight of the sporicidal formulation), more typically from about 0.05 to about 3.7 percent (by weight of the sporicidal formulation), and more typically from about 0.1 to about 2.5 percent (by weight of the sporicidal formulation).

As described above, the sporicidal formulation requires a water soluble oxidant to provide the synergistic effect. Suitable water soluble oxidants are selected from hydrogen peroxide, hypochlorous acid, chlorine, hypoiodous acid, hypobromite, hypobromous acid, bromine, iodine, chlorine dioxide, ozone, superoxide, electrolyzed water, ammonium persulfate, potassium bromate, potassium caroate (Mixture of potassium monopersulfate, potassium sulphate, and potassium bisulfate), potassium chlorate, potassium monopersulfate, potassium persulfate, polyvinylpyrrolidone hydrogen peroxide, sodium bromate, sodium caproylethylformyl benzenesulfonate, sodium carbonate peroxide, sodium chlorate, sodium iodate, sodium perborate, sodium persulfate, urea peroxide, and combinations thereof. In one desirable sporicidal formulation, the water soluble oxidant is hydrogen peroxide.

Typically, the sporicidal formulation contains a water soluble oxidant in an amount from about 0.5 to about 4 percent (by weight of the sporicidal formulation), more typically from about 0.5 to about 3 percent (by weight of the sporicidal formulation), and more typically from about 0.5 to about 2.5 percent (by weight of the sporicidal formulation).

As described above, the sporicidal formulation requires a water insoluble oxidant to provide the synergistic effect. Suitable water insoluble oxidants are selected from benzoyl peroxide, lauroyl peroxide, cumene hydroperoxide, dibenzoyl peroxide, t-butyl benzoyl peroxide, ergosterol endoperoxide, strontium peroxide, ozonized turpentine, magnesium peroxide, and combinations thereof. In one desirable sporicidal formulation, the water insoluble oxidant is benzoyl peroxide.

Typically, the sporicidal formulation contains a water insoluble oxidant in an amount from about 0.1 to about 6 percent (by weight of the sporicidal formulation), more typically from about 0.1 to about 3 percent (by weight of the sporicidal formulation), and more typically from about 0.1 to about 2 percent (by weight of the sporicidal formulation).

Suitable solvents for use in the sporicidal formulation may include, but are not limited to, ethanol, dimethyl isosorbide, isopropanol, ethoxydiglycol, water and acetone. In one desirable sporicidal formulation, the solvent is ethanol. Typically, the sporicidal formulation contains a solvent in an amount from about 0.5 to about 95 percent (by weight of the sporicidal formulation).

Suitable organic acids for use in the sporicidal formulation may include, but are not limited to, benzoic acid, malic acid, lactic acid, citric acid, propionic acid, acetic acid, and combinations thereof. In one desirable sporicidal formulation, the organic acid may be benzoic acid. Typically, the sporicidal formulation contains an organic acid in an amount from about 0.1 to about 5 percent (by weight of the sporicidal formulation).

Suitable peroxide stabilizers for use in the sporicidal formulation may include, but are not limited to, etidronic acid, sodium pyrophosphate, sodium hexametaphosphate, pentasodium diethylenetriaminepentaacetate, ethylenediaminetetraacetic acid, allymethyacrylates copolymer, and combinations thereof. In one desirable sporicidal formulation, the peroxide stabilizers may be etidronic acid. Typically, the sporicidal formulation contains a peroxide stabilizer in an amount from about 0.05 to about 5 percent (by weight of the sporicidal formulation).

Optionally, the sporicidal formulation may also contain botanicals or botanical-derived ingredients that demonstrate sporicidal activity. Example botanicals or botanical-derived ingredients may be selected from *Garcinia morella*, *Thalictrum baicalense*, *Baphicacanthus cusia*, *Setaria italica*, eucalypti leaves, *Litsea cubeba*, *Berberis vernae*, *Salvia miltiorrhiza*, *Coptis teeta*, *Coptis chinensis*, *Psoralea corylifolia*, gambogic acid, neogambogic acid and cryptotanshinone.

Additional optional ingredients for use in the sporicidal formulation may include germination blockers or enhancers. A suitable germination blocker may include, but is not limited to, chenodeoxycholate. Suitable germination enhancers may include, but are not limited to, salts of taurocholic acid, salts of cholic acid, and glycine.

The sporicidal formulation exhibits at least a 90 percent reduction of viable spores within about five minutes of application of said cleaning medium using the sporicidal efficacy test described herein. Other efficacy tests, including those on skin and hard surfaces, may also be employed to demonstrate at least a 90 percent reduction in viable spores within about five minutes.

As noted above, the sporicidal formulation may be incorporated into compositions and wipes to improve the sporicidal efficacy of these products. Generally, the wipes including the sporicidal formulation can be wet wipes or dry wipes. As used herein, the term "wet wipe" means a wipe that includes greater than about 70 percent (by weight substrate) moisture content. As used herein, the term "dry wipe" means a wipe that includes less than about 10 percent (by weight substrate) moisture content. Specifically, suitable wipes for use of the sporicidal composition described herein can include wet wipes, dry wipes, hand wipes, face wipes, cosmetic wipes, household wipes, industrial wipes, and the like. Particularly preferred wipes are wet wipes, and other wipe-types that include a solution.

Materials suitable for the substrate of the wipes are well known to those skilled in the art, and are typically made from a fibrous sheet material which may be either woven or nonwoven. For example, suitable materials for use in the wipes may include nonwoven fibrous sheet materials which include meltblown, coform, air-laid, bonded-carded web materials, hydroentangled materials, and combinations thereof. Such materials can contain synthetic or natural fibers, or a combination thereof. Typically, the wipes define a basis weight of from about 25 to about 120 grams per square meter and desirably from about 40 to about 90 grams per square meter.

In one particular embodiment, the wipes may be a coform basesheet of polymer fibers and absorbent fibers having a basis weight of from about 45 to about 80 grams per square meter and desirably about 60 grams per square meter. Such coform basesheets are manufactured generally as described in U.S. Pat. No. 4,100,324, issued to Anderson, et al.; U.S. Pat. No. 5,284,703, issued to Everhart, et al.; and U.S. Pat. No. 5,350,624, issued to Georger, et al., which are incorporated by reference to the extent to which they are consistent herewith. Typically, such coform basesheets contain a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated PLTD-1810, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials, or combinations thereof, may alternatively be utilized as known to those skilled in the art.

The coform basesheet additionally may contain various absorbent cellulosic fibers, for example, wood pulp fibers. Suitable commercially available cellulosic fibers for use in the coform basesheets can include, for example, NF 405, which is a chemically treated bleached southern softwood Kraft pulp, available from Weyerhaeuser Co. (Federal Way, Wash.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may contain from about 10 to about 90 percent (by weight substrate), desirably from about 20 to about 60 percent (by weight substrate), and more desirably from about 25 to about 35 percent (by weight substrate) of the polymeric meltblown fibers based on the dry weight of the coform basesheet being used to provide the wipes.

In another embodiment, the wipe substrate may be an airlaid nonwoven fabric. The basis weights for airlaid nonwoven fabrics may range from about 20 to about 200 grams per square meter with staple fibers having a denier of about 0.5-10 and a length of about 6 to about 15 millimeters. Wet wipes may generally have a fiber density of about 0.025 to about 0.2 g/cc. Wet wipes may generally have a basis weight of about 20 to about 150 grams per square meter. More desirably the basis weight may be from about 30 to about 90 grams per square meter. Even more desirably the basis weight may be from about 50 about 75 grams per square meter.

Processes for producing airlaid nonwoven basesheets are described in, for example, published U.S. Pat. App. No. 2006/0008621, herein incorporated by reference.

In an alternative embodiment, the wipes may be a composite which includes multiple layers of materials. For example, the wipes may include a three layer composite which includes an elastomeric film or meltblown layer between two coform layers as described above. In such a configuration, the coform layers may define a basis weight of from about 15 to about 30 grams per square meter and the elastomeric layer may include a film material such as a polyethylene metallocene film. Such composites are manufactured generally as described in U.S. Pat. No. 6,946,413, issued to Lange, et al., which is hereby incorporated by reference to the extent it is consistent herewith.

As mentioned above, one type of wipe suitable for use in combination with the sporicidal formulation is a wet wipe. In addition to the wipe substrate, wet wipes also contain a liquid composition. The liquid composition can be any liquid, which can be absorbed into the wet wipe basesheet and may include any suitable components, which provide the desired wiping properties. For example, the components may include water, emollients, surfactants, fragrances, preservatives, organic or inorganic acids, chelating agents, pH buffers, or combinations thereof, as are well known to those skilled in the art. Further, the liquid may also contain lotions, medicaments, and/or antimicrobials.

The wet wipe composition may desirably be incorporated into the wipe in an add-on amount of from about 10 to about 600 percent (by weight of the treated substrate), more desirably from about 50 to about 500 percent (by weight of the treated substrate), even more desirably from about 100 to about 400 percent (by weight of the treated substrate), and especially more desirably from about 200 to 300 percent (by weight of the treated substrate).

The desired liquid composition add-on amounts may vary depending on the composition of the wipe substrate. Typically, however, for coform basesheets, the composition add-on amount will be from about 250 to about 350 percent (by weight of the treated substrate), and more typically about 330 percent (by weight of the treated substrate). For air-laid basesheets, the composition add-on amount will typically be from about 200 to about 300 percent (by weight of the treated substrate), and more typically will be about 235 percent (by weight of the treated substrate).

These add-on amounts will preferably result in a wet wipe comprising sporicidal formulation in an add-on amount of from about 1 to about 5 percent (by weight of the treated substrate), and more preferably from about 1.65 to about 4.95 percent (by weight of the treated substrate).

In another embodiment, the wipe is a dry wipe. In this embodiment, the wipe can be wetted with an aqueous solution just prior to, or at the point of, use of the wipe. The aqueous solution can be any aqueous solution known in the art to be suitable for use in wipe products. The sporicidal formulation may be present in the aqueous solution used to wet the dry wipe prior to use.

Alternately, the dry wipe may be prepared by applying by any suitable means (e.g., spraying, impregnating, etc.) a composition comprising a sporicidal formulation described herein onto a wipe substrate. The composition may contain 100 percent of the sporicidal formulation, or alternately, the sporicidal formulation may be present in the composition in combination with a carrier. In embodiments where the sporicidal formulation used to prepare the dry wipe contains water or moisture, the resulting treated substrate is then dried so that the wipe contains less than about 10 percent (by weight substrate) moisture content, and a dry wipe is produced. The treated substrate can be dried by any means known to those skilled in the art including, for example by use of convection ovens, radiant heat sources, microwave ovens, forced air ovens, and heated rollers or cans, or combinations thereof.

The dry wipe may contain the sporicidal formulation in an add-on amount composition of from about 40 to about 250 percent (by weight of the treated substrate), more desirably about 100 percent (by weight of the treated substrate).

The wipe substrate incorporating the sporicidal formulation described herein may be used to clean various different kinds of surfaces either in a clinical or other type of setting. These may include, for instance, various desk, table or countertops or other parts of furniture surfaces, bath and lavatory surfaces, floor and wall surfaces, medical instruments or devices, or even human skin or bedding and linens. In a liquid form, the sporicidal formulation may be employed in bath or rinse to wash medical instruments, linens, bedclothes, or human skin. The sporicidal formulation may even be incorporated and used in a disinfecting or sanitary solution to wash hands or medical instruments.

Test Method
Sporicidal Efficacy Test
Objective:
  To determine the kill rate of solutions of interest against bacterial spores.
Materials:
  1. Test solutions of interest
  2. *Clostridium difficile* ATCC 43593
  3. *Geobacillus stearotherinophilus* CICC 10142

4. Filter sterilized MilliQ water
5. Neutralization broth (prepared according to directions below)
6. Brain Heart Infusion (BHI) agar plates with 0.15% Sodium Taurocholate
7. Tryptic Soy Agar (TSA) plates
8. Taurocholic acid sodium salt hydrate (Sigma-Aldrich T-4009)
9. Phosphate buffered saline (PBS) pH 7.2
10. Fetal Bovine Serum (FBS)
11. Sterile plating beads
12. Sterile Eppendorf vials (1.5 mL)
13. Sterile tubes (15 mL)
14. Pipettes and sterile pipette tips (100 µL and 1000 µL)
15. Incubator capable of 37±3° C.
16. Anaerobic rectangular jar (7 Liter AnaeroPack System commercially available from Mitsubishi Gas Chemical Co.) with 3 GasPak satchels (BD GasPak EZ, #260678)

Procedure:
1. Prepare culture stock of organism of interest to $10^7$ CFU/ml in PBS.
2. Thoroughly vortex the stock culture for 10 minutes at medium-high speed.
3. Dilute a small portion of the stock culture in MilliQ filter sterilized water and add FBS soil load to the inoculum to achieve a concentration of 5% v/v FBS.
4. Place the inoculum in a sonicating water bath for five cycles of one minute on, one minute off.
5. Add 100 µL of spore culture to sterile vial containing 900 µL of test solution and vortex.
6. After the test exposure time, vortex the vials.
7. Transfer 100 µL of test solution and spore mixture to sterile tubes containing 900 µL neutralization broth to neutralize.
8. Place the neutralized samples in a sonicating water bath for five cycles of one minute on, one minute off.
9. Vortex each tube. For *C. difficile*, pipette 100 µL, of each neutralized sample on BHI+0.15% sodium taurocholate media plates (prepared in lab according to dehydrated powder instructions). For *G. stearothermophilus*, pipette 100 µL of each neutralized sample onto TSA plates. Spread using sterile beads.
10. Prepare a control sample by adding the spore culture to 900 µL of filter sterilized MQ water and repeat steps 3-6 above. Dilute control code to achieve $10^2$ CFU/ml.
11. For *C. difficile*, place plates in anaerobic jars or boxes (with appropriate number of catalase pouches) or in the anaerobic chamber and incubate for 48±8 hours at 37±3° C. For *G. stearothermophilus*, incubate plates aerobically for 48±8 hours at 37±3° C.
12. After incubation, enumerate colonies and record results. Calculate $Log_{10}$ reduction by comparing the number of colonies recovered from the test solution versus those recovered with the control.

Neutralization Broth Preparation:
1. Mix the following ingredients:
   1 L Letheen broth
   0.3% ppm Lecithin
   3% ppm Tween 80
   0.1% ppm Histidine
2. Solution is sterilized by autoclave.
3. Catalase (0.1-0.2%) is added when completely cooled and then filter sterilized.

EXAMPLES

Example 1

In this example, a sporicidal formulation was prepared. The following ingredients were used to prepare the sporicidal formulation that illustrates the sporicidal efficacy on both *Clostridium difficile* spores and the representative *Geobacillus stearothermophilus* spores under the Sporicidal Efficacy Test described herein. The effect was demonstrated against both spores illustrating that the formulation would likely be effective against a number of different types of spores.

TABLE 1

Exemplary Formulation A

| Ingredient | Wt. % |
|---|---|
| Ethanol | 65.0 |
| Water | 28.4 |
| Lauramine oxide | 2.5 |
| Hydrogen Peroxide | 2.0 |
| Benzoyl Peroxide | 1.0 |
| Benzoic Acid | 0.5 |
| Etidronic Acid | 0.6 |

In addition, several comparative formulations were prepared based on Exemplary formulation A to illustrate the synergistic effect of the various ingredients. In the comparative solutions, at least one of the ingredients was taken out of Exemplary Formulation A to illustrate how specific ingredients are needed to provide the sporicidal efficacy. Each formulation contained the following ingredients (% w/w) and were qs'ed with water to adjust for ingredients removed to test for the synergistic effect ethanol (65.0%) etidronic acid (0.6%), and benzoic acid (0.5%). Water was also added at a QS to make a 100% formulation as illustrated in Table 2.

TABLE 2

Exemplary Formulations.

| Formulation | Lauramine oxide (2.5% w/w) | Benzoyl peroxide (1% w/w) | Hydrogen peroxide (2% w/w) | $LOG_{10}$ CFU/ml kill of *C. diff.* after 5 minutes | $LOG_{10}$ CFU/ml kill of *G. stearothermophilus* after 5 minutes |
|---|---|---|---|---|---|
| Example Formulation A | x | x | x | 4.9 | 5.1 |
| Comparative Formulation A | | x | x | 4.4 | 3.8 |
| Comparative Formulation B | x | | x | 0 | 0.1 |
| Comparative Formulation C | x | | | 0 | 0 |
| Comparative Formulation D | x | x | | 0 | 0 |

Exemplary Formulation A provides a sporicidal benefit with the amine oxide surfactant, the water soluble oxidant (hydrogen peroxide) and water insoluble oxidant (benzoyl peroxide). Comparative Formulation C contained only the amine oxide and not the water soluble oxidant or the water insoluble oxidant provided no efficacy against spores. Similarly Comparative Formulations 13 and D containing the amine oxide and one of the water soluble oxidant or the water insoluble oxidant provided no efficacy against the two spores.

Comparative Formulation A does not contain the amine oxide surfactant. While Comparative Formulation A did provide a sporicidal efficacy, it does not provide the same level of efficacy as Example Formulation A. This is unexpected since the Comparative Formulations C containing only the amine oxide surfactant provided no efficacy. However, the synergistic effect of the combination of an amine oxide surfactant with a water soluble oxidant (hydrogen peroxide) and a water insoluble oxidant (benzoyl peroxide) illustrates better efficacy.

Example 2 (Comparative)

Additional comparative formulations were prepared based on the Exemplary Formulation A found in Table 1, but containing more than 2.5 wt. % (based on the weight of the formulation) of lauramine oxide. A formulation containing 3.7 percent lauramine oxide illustrated reduced sporicidal activity as compared to Exemplary Formulation A, illustrating the importance that a certain range of an amine oxide surfactant is necessary to provide optimal sporicidal activity of the formulation.

TABLE 3

Exemplary Formulations

| % w/w lauramine oxide | $LOG_{10}$ CFU/ml kill of *G. stearothermophilus* after 5 minutes |
|---|---|
| 2.5 | >4.0 |
| 3.7 | 2.8 |

Other modifications and variations to the appended claims may be practiced by those of ordinary skill in the art, without departing from the spirit and scope as set forth in the appended claims. It is understood that features of the various examples may be interchanged in whole or part. The preceding description, given by way of example in order to enable one of ordinary skill in the art to practice the claimed invention, is not to be construed as limiting the scope of the invention, which is defined by the claims and all equivalents thereto.

The invention claimed is:

1. A sporicidal formulation comprising:
    a solvent;
    about 0.05 to about 3.7 percent (by weight of the formulation) of an amine oxide surfactant, wherein the amine oxide surfactant is lauramine oxide;
    about 0.5 to about 4 percent (by weight of the formulation) of a water soluble oxidant, wherein the water soluble oxidant is hydrogen peroxide; and
    about 0.1 to about 6 percent (by weight of the formulation) of a water insoluble oxidant, wherein the water insoluble oxidant is benzoyl peroxide.

2. The sporicidal formulation of claim 1 wherein the formulation comprises from about 0.1 to about 2.5 percent (by weight of the formulation) of the amine oxide surfactant.

3. The sporicidal formulation of claim 1 further comprising an organic acid wherein the organic acid is selected from the group consisting of benzoic acid, malic acid, lactic acid, citric acid, propionic acid, acetic acid, and combinations thereof.

4. The sporicidal formulation of claim 1 wherein the solvent is selected from the group consisting of ethanol, dimethyl isosorbide, isopropanol, ethoxydiglycol, water, acetone, and combinations thereof.

5. The sporicidal formulation of claim 1 further comprising a peroxide stabilizer wherein the peroxide stabilizer is selected from the group consisting of etidronic acid, sodium pyrophosphate, sodium hexametaphosphate, pentasodium diethylenetriaminepentaacetate, ethylenediaminetetraacetic acid, allymethyacrylates copolymer, and combinations thereof.

6. A wipe comprising:
    a wipe substrate; and
    a sporicidal formulation comprising:
    a solvent;
    about 0.05 to about 3.7 percent (by weight of the formulation) of an amine oxide surfactant, wherein the amine oxide surfactant is lauramine oxide;
    about 0.5 to about 4 percent (by weight of the formulation) of a water soluble oxidant, wherein the water soluble oxidant is hydrogen peroxide; and
    about 0.1 to about 6 percent (by weight of the formulation) of a water insoluble oxidant, wherein the water insoluble oxidant is benzoyl peroxide.

7. The wipe of claim 6 wherein the composition comprises from about 0.1 to about 2.5 percent (by weight of the formulation) of the amine oxide surfactant.

8. The wipe of claim 6 further comprising an organic acid wherein the organic acid is selected from the group consisting of benzoic acid, malic acid, lactic acid, citric acid, propionic acid, acetic acid, and combinations thereof.

9. The wipe of claim 6 wherein the solvent is selected from the group consisting of ethanol, dimethyl isosorbide, isopropanol, ethoxydiglycol, water, acetone, and combinations thereof.

10. The wipe of claim 6 further comprising a peroxide stabilizer wherein the peroxide stabilizer is selected from the group consisting of etidronic acid, sodium pyrophosphate, sodium hexametaphosphate, pentasodium diethylenetriaminepentaacetate, allymethyacrylates copolymer, and combinations thereof.

* * * * *